United States Patent
Nagrodsky et al.

(10) Patent No.: US 10,324,067 B2
(45) Date of Patent: Jun. 18, 2019

(54) VIBRATION MONITORING SYSTEM AND METHOD

(71) Applicant: ALSTOM TRANSPORT TECHNOLOGIES, Saint-Ouen (FR)

(72) Inventors: Nicholas David Nagrodsky, Melbourne, FL (US); James Michael Kiss, Jr., Melbourne, FL (US); Jeffrey Fries, Grain Valley, MO (US); Derick Diaz, Melbourne, FL (US); David Farmer, Melbourne, FL (US)

(73) Assignee: Alstom Transport Technologies, Saint-Ouen (FR)

( * ) Notice: Subject to any disclaimer, the term of this patent is extended or adjusted under 35 U.S.C. 154(b) by 72 days.

(21) Appl. No.: 15/889,972

(22) Filed: Feb. 6, 2018

(65) Prior Publication Data
US 2018/0156757 A1   Jun. 7, 2018

Related U.S. Application Data

(63) Continuation-in-part of application No. 15/153,525, filed on May 12, 2016.
(Continued)

(51) Int. Cl.
*G01V 13/00*  (2006.01)
*G01N 29/24*  (2006.01)
*G01M 11/00*  (2006.01)
*G01N 29/12*  (2006.01)
*G01N 29/11*  (2006.01)
*G01N 29/44*  (2006.01)

(52) U.S. Cl.
CPC ......... *G01N 29/2418* (2013.01); *G01M 11/30* (2013.01); *G01N 29/11* (2013.01); *G01N 29/12* (2013.01); *G01N 29/4463* (2013.01); *G01N 2291/01* (2013.01); *G01N 2291/2623* (2013.01)

(58) Field of Classification Search
CPC ...................................................... G01V 13/00
USPC ......... 73/1.85, 570, 579, 584, 636; 367/118, 367/124–130; 356/3, 243.1, 614, 256
See application file for complete search history.

(56) References Cited

U.S. PATENT DOCUMENTS 3,609,350 A  *  9/1971  Wilson .................... B61L 17/00
                                                        104/26.2
6,254,385 B1    7/2001  Jung et al.
7,197,199 B2    3/2007  Cuypers et al.

FOREIGN PATENT DOCUMENTS

JP          08072720     *   3/1996

* cited by examiner

*Primary Examiner* — Robert R Raevis
(74) *Attorney, Agent, or Firm* — Knobbe, Martens, Olson & Bear, LLP

(57) ABSTRACT

A method detects the presence of a vehicle on a railway track using a sensing processor monitoring a sensing system for detecting vibration into ground installed along the railway track. The sensing system includes a detection module for detecting a vehicle on the railway track. The method includes an initialization step which includes the sub-steps of emitting a first signal to be received by the sensing processor through the sensing system, sending a first message to the sensing processor, monitoring the sensing system, and configuring the detection module in function of the received first signal and configuration data received in the first message. The configuration data can include location of the initialization device, intensity/magnitude of the first signal, emission time of the first signal, and/or type of object corresponding to the first signal.

21 Claims, 11 Drawing Sheets

Related U.S. Application Data

(60) Provisional application No. 62/161,712, filed on May 14, 2015.

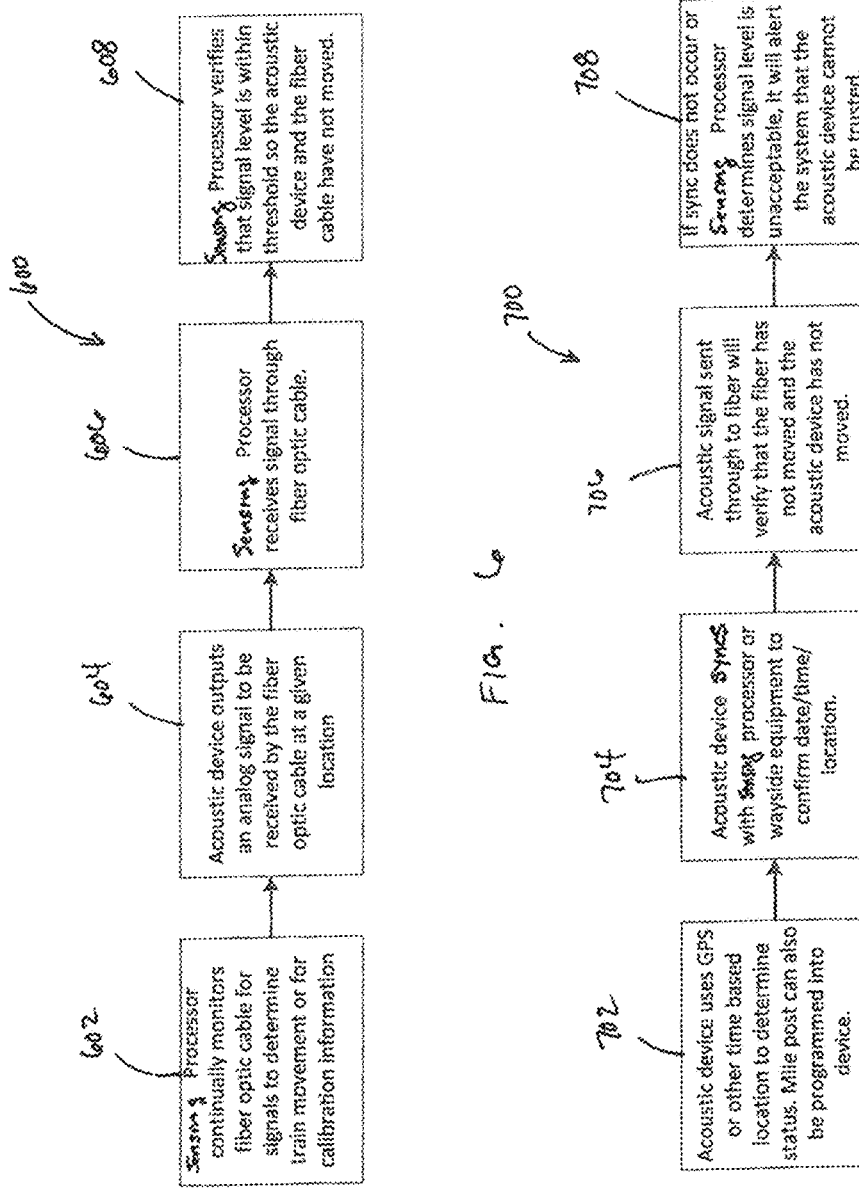

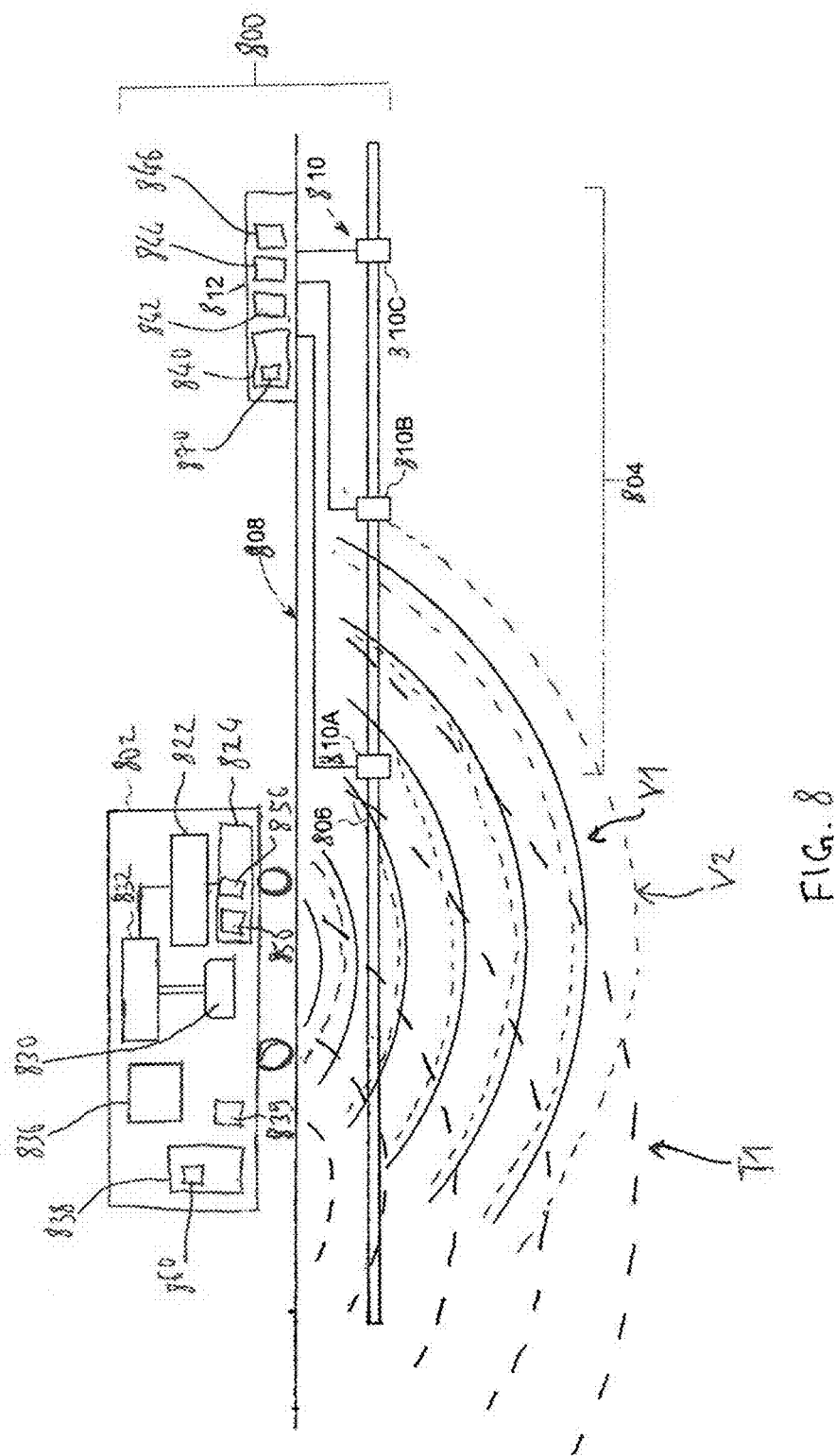

VIBRATION MONITORING SYSTEM AND METHOD

CROSS-REFERENCE TO RELATED APPLICATIONS

This application is a continuation-in-part of U.S. patent application Ser. No. 14/501,177, filed on Sep. 30, 2014, which is hereby incorporated by reference herein in its entirety.

FIELD OF THE INVENTION

Embodiments of the subject matter disclosed herein relate to monitoring systems and methods.

BACKGROUND OF THE INVENTION

Some known systems sense vibrations propagating through the ground in order to detect the presence of one or more objects. These systems can examine the vibrations that are sensed in order to attempt to identify the objects, determine where the objects are located, and the like. One example of such systems senses ground vibrations using a fiber optic cable extending beneath or near rail tracks. While these fiber optic cables may have been placed along the rail track to provide network connectivity, some rail companies have the ability to use these fiber optic cables to monitor vibrations in the ground. These vibrations can be used to attempt to identify the passage of rail vehicles along the track.

One problem with these known systems is that the systems are not "vital" systems. For example, the systems may be unable to automatically correct changes in sensed vibrations that are caused by external factors. Changes in the weather and other factors may change the vibrations and/or the propagation of vibrations through the ground, and can hinder or block the ability of these systems to accurately identify rail vehicles based on the vibrations that are generated. These systems may suffer from incorrectly detecting a rail vehicle based on vibrations that are not caused by the rail vehicle, but that appear to be caused by a rail vehicle due to the impact of environmental conditions on the propagation of the vibrations. Similarly, these systems may suffer from failing to detect a rail vehicle based on vibrations that are caused by the rail vehicle, but that do not appear to be caused by a rail vehicle due to the impact of environmental conditions on the propagation of the vibrations.

Additionally, existing systems typically rely on a one-time calibration of the exact location of the fiber optic cables. Changes in the fiber optic cable or interrogation equipment subsequent to calibration, therefore, can introduce errors into the data utilized to detect vehicles. For example, if the fiber optic cable characteristics or the fiber optic cable itself is moved, data skewing can occur and the accuracy of the system can be affected. Accordingly, there is a need for a system and method that is capable of ensuring that the physic fiber optic cables have not moved, and which can be calibrated to account for any such movements.

Moreover, initial configuration and calibration of the existing systems is complex, time-consuming, which implies that the installation of such systems is very long and requires a lot of time and/or many people on site to configure the system.

BRIEF DESCRIPTION OF THE INVENTION

In one embodiment, the invention concerns a method for detecting the presence of a vehicle on a railway track, using a sensing processor monitoring a sensing system for detecting vibration into ground installed along the railway track and comprising a detection module for detecting a vehicle on the railway track. The method comprises an initialization step comprising the sub-steps of: at an initialization device, emitting a first signal to be received by the sensing processor through the sensing system; at the initialization device, sending to the sensing processor, a first message comprising configuration data chosen among, location of the initialization device, intensity/magnitude of the first signal, emission time of the first signal, type of object corresponding to the first signal; at the sensing processor, monitoring the sensing system; and at the sensing processor, configuring the detection module in function of the received first signal and the received configuration data.

Preferred embodiments of the invention are the subject matter of the dependent claims, whose content is to be understood as forming an integral part of the present description.

In another embodiment of the invention, the method (e.g., for sensing vibrations) includes introducing baseline vibrations into a fiber optic cable with one or more of a designated frequency or a designated amplitude, monitoring changes in the baseline vibrations using the fiber optic cable, and determining information about environmental conditions outside of the fiber optic cable based at least in part on the changes in the baseline vibrations that are monitored.

In another embodiment, the invention concerns a system (e.g., a monitoring system) including a control system and a sensing system. The control system is configured to introduce baseline vibrations into a fiber optic cable with one or more of a designated frequency or a designated amplitude. The sensing system is configured to monitor changes in the baseline vibrations using the fiber optic cable and to determine information about environmental conditions outside of the fiber optic cable based at least in part on the changes in the baseline vibrations that are monitored.

In another embodiment, the invention concerns a sensing system includes one or more sensors and one or more sensing processors. The one or more sensors are configured to examine light traveling through a fiber optic cable extending along and beneath a route traveled by vehicles. The one or more sensing processors are configured to monitor changes in baseline vibrations introduced into the fiber optic cable at designated times, and to determine information about environmental conditions outside of the fiber optic cable based at least in part on the changes in the baseline vibrations that are monitored.

The invention concerns also a detecting system for detecting the presence of a vehicle on a railway track having the features defined in claim 20.

BRIEF DESCRIPTION OF THE DRAWINGS

Reference is made to the accompanying drawings in which particular embodiments and further benefits of the invention are illustrated as described in more detail in the description below, in which:

FIG. 6 illustrates a flowchart of a method for verifying the integrity of the vibration monitoring system shown in FIG. 1;

FIG. 7 illustrates a flowchart of a method for determining the location status of a calibration device of the vibration monitoring system shown in FIG. 1;

FIG. 8 is a schematic diagram of a vibration monitoring system, i.e. of a detecting system for detecting the presence of a vehicle on a railway track according to one embodiment;

DETAILED DESCRIPTION OF THE INVENTION

One or more embodiments of a vibration monitoring system and method are described herein. These systems and methods can generate vibrations that propagate through a portion of the ground that includes one or more sensing cables. The sensing cable can be used to detect the vibrations. As one example, a fiber optic cable can be used as the sensing cable, with changes in refraction of light in the fiber optic cable being representative of the vibrations that propagate through, into, or around the cable. Based on the magnitude (e.g., amplitude), frequency, period, or the like, of the vibrations that are detected, the presence and/or location of one or more objects on the ground can be determined. For example, passage of a vehicle above the sensing cable can be detected, as well as the speed, direction of travel, size, or the like, of the vehicle. Optionally, changes in the vibrations can be used to identify damaged segments of a route being traveled upon by the vehicle.

In one aspect, the vibration monitoring systems and methods can detect vibrations caused by moving objects and determine information about the vibrations and/or objects based on the detected vibrations. This information that is determined can include peaks, waveforms, frequencies, amplitudes, or the like, in a frequency spectrum of the vibrations, or other information. This information can be used to identify the moving object, determine a location of the moving object, determine a speed of the object, identify a portion of a route being traveled on by the object that may be damaged, or the like.

The vibrations may change due to factors other than the moving objects (e.g., moving vehicles, damaged routes, or the like). For example, in different environmental conditions (e.g., different times, seasons, periods of condensation, etc.), the same object may cause the vibration monitoring systems and methods to detect different vibrations. The differences between the detected vibrations can be caused by the changing environmental conditions instead of the object of interest. The systems and methods can identify these differences caused by the environmental conditions and modify the information that is determined based on the detected vibrations to account for the changes caused by the environmental conditions. The systems and methods can therefore self-correct changes in the vibrations that are not caused by the objects of interest in order to improve the vitality, accuracy, precision, and functionality of the systems and methods.

Embodiments of the present invention may be used with a variety of vehicles, including rail vehicles, mining vehicles, OHVs, automobiles and the like. The vehicles may utilize internal combustion engines, electricity, a hybrid of the two, or other power sources. The vehicles may be automated, self-guided or may be guided via operator input.

Figure 1:
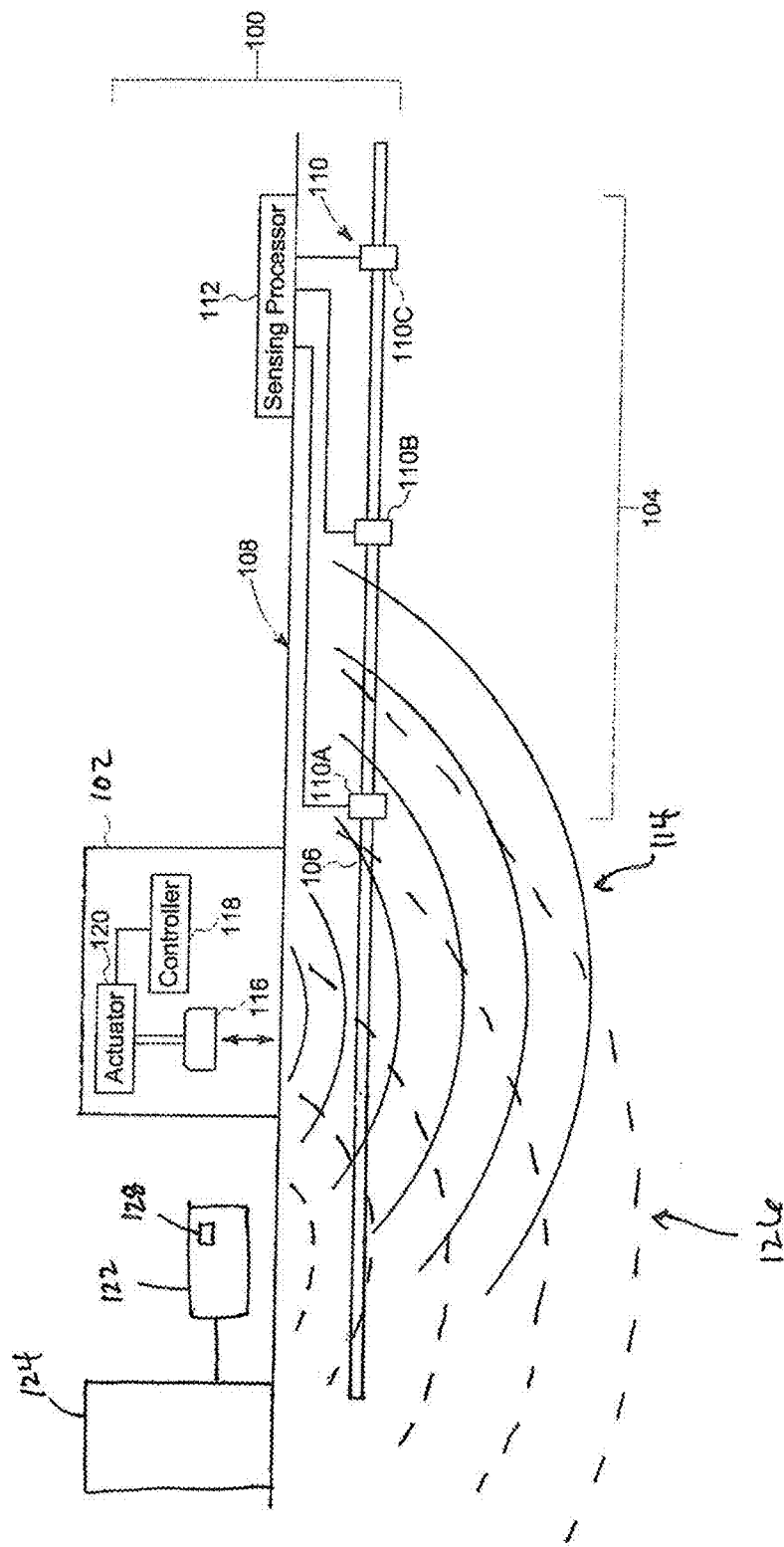
FIG. 1 is a schematic diagram of a vibration monitoring system, i.e. of a detecting system for detecting the presence of a vehicle on a railway track according to one embodiment.

FIG. 1 is a schematic diagram of a vibration monitoring system 100, i.e. of a detecting system for detecting the presence of a vehicle on a railway track, according to one embodiment. The system 100 includes a control system 102 that generates baseline vibrations that are used to detect changing environmental conditions. The system 100 also includes a sensing system 104 that detects vibrations caused by objects of interest (e.g., vibrations of interest) and the baseline vibrations. Optionally, the system 100 may include multiple sensing systems 104 that separately detect the vibrations of interest or the baseline vibrations.

A sensing device 106 is disposed beneath a surface 108 of the ground (e.g., the surface of the earth or another surface). In one embodiment, the sensing device 106 is a fiber optic cable that communicates information between two or more locations by internally refracting light within the device 106. Alternatively, the sensing device 106 may be another type of cable that can be used to detect vibrations in the ground. The sensing system 104 includes several sensors 110 (e.g., sensors 110A-C) operably connected with the sensing device 106 at different locations. For example, the sensors 110 may be light-sensitive devices that measure changes in how light is internally reflected or otherwise refracted in the sensing device 106. The number and arrangement of the sensors 110 is provided merely as one example. As described herein, the sensing device 106 can be used to sense vibrations propagating through the ground. Alternatively, another device, system, or apparatus may be used as the sensing device 106 to detect the vibrations. For example, one or more accelerometers, seismometers, or the like, may sense the vibrations.

A sensing processor 112 represents one or more computer processors (e.g., microprocessors) and advantageously an associated memory, hardware circuits or circuitry, or a combination thereof, that examine data that is output by the sensors 110 to measure the vibrations propagating through the sensing device 106. For example, the sensors 110 may be conductively coupled with the sensing processor 112 by one or more wires, cables, or the like, and/or may be wirelessly connected with the sensing processor 112 such that the sensors 110 can communicate data representative of the vibrations detected using the sensing device 106 to the sensing processor 112.

The sensing processor 112 examines the data received from the sensors 110 to identify the vibrations propagating through, into, and/or around the sensing device 106. Based on these vibrations and/or changes in the vibrations, the sensing processor 112 can determine information about an object on the surface 108. This information can include an identification of the object of interest on the surface 108, a location of a moving object of interest on the surface 108, a moving speed of the object of interest, a size of the object of interest, or the like. For example, different objects, different locations of the objects, different speeds of the objects, and/or different sizes of the objects may be associated with different patterns or waveforms of the vibrations that are determined by the sensing processor 112 and detected using the sensing device 106.

In order to account for changes in environmental conditions and the impact of these changes in the vibrations caused by objects of interest, the control system 102 can generate baseline vibrations into the ground where the sensing device 106 is located. These baseline vibrations may be generated at pre-designated times and/or during pre-designated time periods. The baseline vibrations may be generated with pre-designated amplitudes and/or frequencies. As described below, these baseline vibrations may be detected by the sensing system 104 and used to modify and correct changes to vibrations of interest that are caused by environmental conditions.

Figure 2:
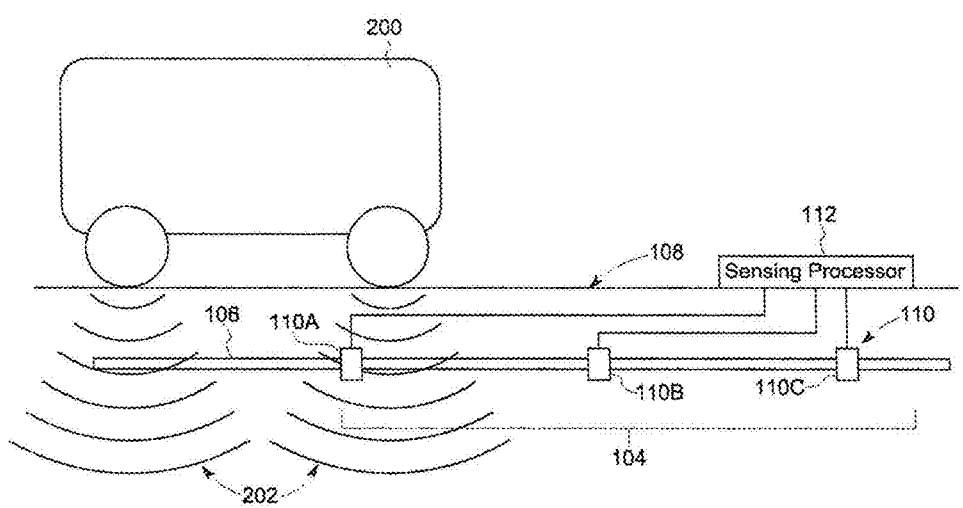
FIG. 2 schematically illustrates a sensing system of the detecting system shown in FIG. 1 during movement of an object of interest according to one embodiment.

FIG. 2 schematically illustrates the sensing system 104 of the vibration monitoring system 100 shown in FIG. 1 during movement of an object of interest 200 according to one embodiment. The object of interest 200 is shown as a vehicle, such as a rail vehicle, automobile, mining vehicle, or the like, but alternatively may be another object. For example, the sensing device 106 can extend along a route, such as a railway track, for sensing vibrations generated by a vehicle, such as a rail vehicle, traveling along the route. During movement of the object of interest 200 on or near the surface 108, vibrations of interest 202 are generated in the ground beneath the surface 108. The vibrations of interest are vibrations that differ from baseline vibrations, as described herein. These vibrations of interest 202 propagate through the ground to the sensing device 106. The vibrations of interest 202 can change the manner in which light is reflected within the sensing device 106. These changes are detected by the sensors 110 as changes in intensities of light, changes in intensities of light at different wavelengths, or the like. The sensors 110 output data representative of the light and/or changes in the manner in which the light is reflected within the sensing device 106. This data is communicated to the sensing processor 112.

Figure 3:
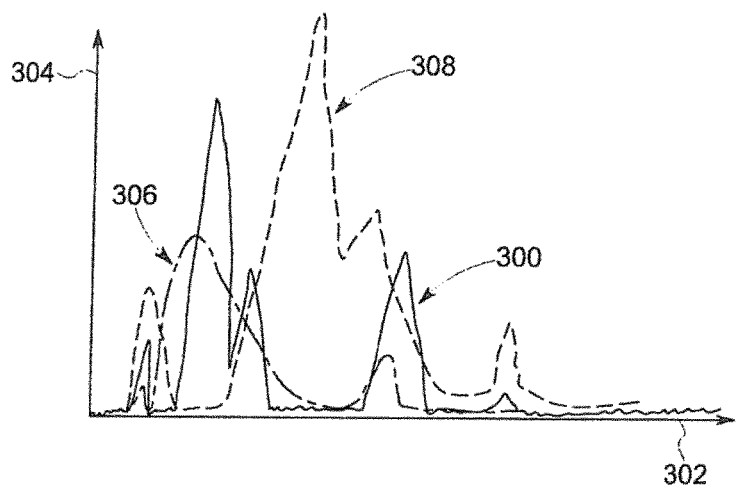
FIG. 3 illustrates one example of a frequency spectrum of vibrations of interest generated by movement of the object of interest shown in FIG. 2 as detected by the sensing system shown in FIG. 1.

FIG. 3 illustrates one example of a frequency spectrum of vibrations of interest 300 generated by movement of the object of interest 200 shown in FIG. 2 as detected by the sensing system 104. The vibrations of interest 300 are shown alongside a horizontal axis 302 representative of frequencies of the vibrations of interest 300 and a vertical axis 304 representative of amplitude or magnitude of the vibrations of interest 300 at the different frequencies.

The vibrations of interest 300 can represent the vibrations detected by the sensing system 104 during movement of the object of interest 200. These vibrations of interest 300 can represent a signature or waveform that is associated with the object of interest 200. When the vibrations of interest 300 are detected, the object of interest 200 can be identified by the sensing processor 112 by comparing the vibrations of interest 300 to different signatures or waveforms that are associated with different objects of interest 200, and identifying the object of interest 200 based on this comparison. For example, the signatures or waveforms may be defined as designated peaks in the vibrations of interest 300 that are located at designated frequencies and/or within a designated range of frequencies. If the vibrations of interest 300 have peaks in the designated frequencies and/or designated range of frequencies, then the vibrations of interest 300 may be identified as the object of interest 200 that is associated with the designated frequencies and/or designated range of frequencies of the signature or waveform. Optionally, different objects of interest 200 may be associated with different signatures or waveforms, different speeds of different objects of interest 200 may be associated with different signatures or waveforms, different locations of objects of interest 200 may be associated with different signatures or waveforms, and the like, so that the sensing system 104 may be able to identify different objects of interest 200, different speeds of objects of interest 200, different locations of the objects of interest 200, and the like.

The sensing processor 112 may not be able to identify the object of interest 200 due to changes in environmental conditions, however. For example, the density, makeup, mass, or the like, of the ground may change at different times of the day, during different seasons, and during different weather conditions (e.g., rain, snow, ice, dry weather, etc.). These different environmental conditions can impact the manner in which the vibrations of interest 202 (shown in FIG. 2) propagate through the ground and are detected by the sensing system 104.

For example, during first environmental conditions (e.g., dry weather during daylight of a summer month), the vibrations of interest may appear as the vibrations of interest 300 shown in FIG. 3. But, during different, second environmental conditions (e.g., wet weather during the night of a spring month), the same object of interest 200 may generate the vibrations of interest that are detected by the sensing system 104 as vibrations of interest 306 in FIG. 3. During different, third environmental conditions (e.g., ice on the ground during the winter), the same object of interest 200 may generate the vibrations of interest that are detected by the sensing system 104 as vibrations of interest 308 in FIG. 3. The changing environmental conditions can prevent the sensing system 104 from being able to accurately identify the object of interest 200 based on the vibrations that are detected.

Returning to the description of the vibration monitoring system 100 shown in FIG. 1, the system 100 can adapt to changes in the environmental conditions by repeatedly monitoring changes in baseline vibrations generated by the system 100 and using these changes to modify (e.g., correct) the information that is determined from the vibrations of interest generated by the objects 200 (shown in FIG. 2). The control system 102 may generate baseline vibrations 114 in the ground by moving a weighted object 116 relative to the ground. The weighted object 116 can be a weight, a body with a moveable eccentric mass, or another type of body that can generate vibrations in the ground when moved relative to the ground. The weighted object 116 shown in FIG. 1 can be moved toward the surface 108 of the ground to strike the ground and generate the baseline vibrations 114. The weighted object 116 can then be moved away from the ground for preparation in striking the ground again to generate additional baseline vibrations 114.

The control system 102 includes a controller 118 that represents one or more computer processors (e.g., microprocessors), hardware circuits or circuitry, or a combination thereof. The controller 118 controls generation of the baseline vibrations 114 by controlling movement of the object 116. An actuator 120 moves the object 116 pursuant to instruction signals received from the controller 116. The actuator 120 can include a motor, electromagnet, pneumatically controlled piston, or another device capable of moving the object 116 to generate the baseline vibrations 114. The controller 118 generates the instruction signals and communicates the signals to the actuator 120 via one or more wired and/or wireless connections. The signals can indicate the times at which the actuator 120 is to move the object 116 to generate the baseline vibrations 114, how long of a time period that the actuator 120 is to generate the baseline vibrations 114, and/or how to move the object 116 to generate the baseline vibrations 114. With respect to instructions on how to move the object 116, these instructions can tell the actuator 120 how high to lift the object 116 off the surface 108 before dropping or moving the object 116 toward the surface 108, how quickly to move the object 116 toward the surface 108 (or whether to drop the object 116 onto the surface 108), how many times to move the object 116, and/or how frequently the object 116 should be moved. If the object 116 is to be dropped onto or otherwise moved into contact with the surface 108 or another object in contact with the surface 108 to generate the baseline vibrations 114, then the instructions can dictate how fast the object 116 is moved toward the surface 108 or other object, how far the object 116 is away from the surface 108 when the object 116 is dropped or moved toward the surface 108, and the like. If the object 116 is moved relative to the surface 108 without striking the surface 108 or an object on the surface 108 (e.g., the object 116 is an eccentric mass that is rotated or otherwise moved relative to the surface 108 to generate the baseline vibrations 114), then the instructions can dictate how rapidly the object 116 is moved, how long the object 116 is moved, or the like.

Figure 4:
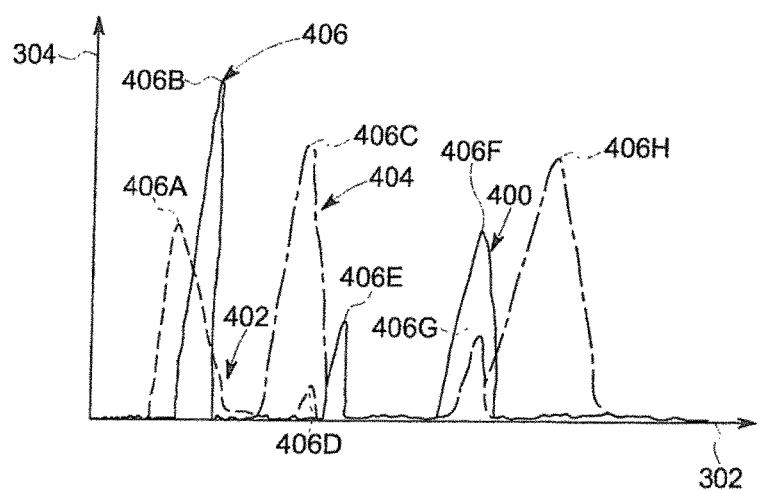
FIG. 4 illustrates a frequency spectrum of baseline vibrations generated by a control system shown in FIG. 1 during different environmental conditions according to one embodiment.

FIG. 4 illustrates a frequency spectrum of baseline vibrations 400, 402, 404 generated by the control system 102 shown in FIG. 1 during different environmental conditions according to one embodiment. The baseline vibrations 400, 402, 404 are shown alongside the horizontal and vertical axes 302, 304 described above in connection with FIG. 3. The baseline vibrations 400, 402, 404 are generated by the control system 102 by moving the same object 116 (shown in FIG. 1) in the same manner, but at different times and under different environmental conditions. For example, the baseline vibrations 400 may be sensed by the sensing system 104 responsive to a ten pound (or 4.5 kilogram) object 116 being dropped onto the surface 108 (shown in FIG. 1) from one foot (or thirty centimeters) above the surface 108 during dry conditions during the daytime. The baseline vibrations 402, 404 may be generated and sensed during other conditions. For example, the baseline vibrations 402 may be generated by dropping the same ten pound (or 4.5 kilogram) object 116 being onto the surface 108 from one foot (or thirty centimeters) above the surface 108 during rain, when there is snow on the surface 108, during nighttime, or the like. The baseline vibrations 404 may be generated by dropping the same ten pound (or 4.5 kilogram) object 116 being onto the surface 108 from one foot (or thirty centimeters) above the surface 108 when there is ice on the surface 108.

The control system 102 can generate the baseline vibrations at designated times, such as times that are known to the sensing system 104. The control system 102 can generate the baseline vibrations at times that are known or communicated to the sensing system 104 (e.g., by the controller 118 of the control system 102 or another device) so that the sensing system 104 can differentiate between baseline vibrations and vibrations of interest.

In one aspect, the sensing processor 112 can determine that the system 100 is malfunctioning based at least in part on the baseline vibrations. For example, the sensing processor 112 may be aware of the times at which the baseline vibrations are generated by the control system 102. If the sensing processor 112 does not detect the baseline vibrations at times that correspond to when the baseline vibrations are generated, then the sensing processor 112 can determine that the system 100 is malfunctioning. Responsive to determining this, the sensing processor 112 can communicate one or more warning signals to another location, such as a repair facility, dispatch facility, or the like, to warn of the malfunction of the system 100, and/or to request inspection, repair, maintenance, or the like, of the system 100.

The baseline vibrations 400 can be designated as a calibration signature. The sensing system 104 may periodically, regularly, randomly, or otherwise repeatedly re-determine the baseline vibrations that are used as the calibration signature. Subsequently obtained baseline vibrations 402, 404 can be compared to the calibration signature in order to determine how the vibrations sensed by the sensing system 104 change, due to the changing environmental conditions. For example, the sensing system 104 can sense the baseline vibrations 402 and compare the baseline vibrations 402 to the baseline vibrations 400 by comparing characteristics of the vibrations 400, 402 with each other. These characteristics can include, but are not limited to, locations (e.g., frequencies) of peaks 406 (e.g., peaks 406A-H), widths of the peaks 406 (e.g., the ranges of frequencies over which one or more peaks 406 extend, heights of peaks 406 (e.g., the amplitude of one or more of the peaks 406 along the vertical axis 304), and the like.

In the illustrated example, the sensing system 104 can compare the baseline vibrations 400, 402 and determine that the peak 406B in the baseline vibration 400 has moved to a lower frequency and/or has a reduced amplitude as the peak 406A in the baseline vibration 402, that the peak 406E in the baseline vibration 400 has moved to a lower frequency and/or has a reduced amplitude as the peak 406D in the baseline vibration 402, and/or that the peak 406F in the baseline vibration 400 has the same or similar frequency as the peak 406G (e.g., is within a designated range of the peak 406F, such as 1%, 5%, 10%, or the like) and/or has a reduced amplitude as the peak 406G in the baseline vibration 402.

The sensing system 104 can use these differences between the baseline vibrations 400, 402 to correct the information about the objects 200 that is determined from the vibrations of interest 300, 306, 308 shown in FIG. 3. For example, due to changing environmental conditions, the baseline vibrations 400, 402 appear to shift to lower frequencies and/or have reduced amplitudes, as described above. To correct for the impact of the changing environmental conditions on the vibrations of interest, the sensing system 104 can measure frequencies and/or amplitudes from the vibrations of interest, and then modify these frequencies and/or amplitudes. For example, the sensing system 104 can increase the value of the measured frequencies at which peaks appear in the vibrations of interest 300, 306, 308, can increase the value of the amplitudes of the peaks in the vibrations of interest 300, 306, 308, or the like. The frequencies and/or amplitudes of the peaks in the vibrations of interest 300, 306, 308 can be increased by the same amount that the frequencies and/or amplitudes of the peaks in the baseline vibrations 400, 402 decreased, or may be increased by an amount that is at least partially based on the decrease in the peaks in the baseline vibrations 400, 402. While the sensing system 104 may not be actually changing the frequencies, amplitudes, or the like, of the peaks, the sensing system 104 can change the measured frequencies, amplitudes, or the like, that are measured from the vibrations of interest and used to identify information about the object 200.

As another example, the sensing system 104 can compare the baseline vibrations 400, 404 and determine that the peak 406B in the baseline vibration 400 has moved to a higher frequency and/or has a reduced amplitude as the peak 406C in the baseline vibration 404, and/or that the peak 406F in the baseline vibration 400 has moved to a higher frequency and/or has an increased amplitude as the peak 406H in the baseline vibration 404. The sensing system 104 can use these differences between the baseline vibrations 400, 404 to correct information determined from the vibrations of interest 300, 306, 308 shown in FIG. 3. For example, due to changing environmental conditions, the baseline vibrations 400, 402 appear to shift to higher frequencies and/or have increased amplitudes, as described above. To correct for the impact of the changing environmental conditions on the vibrations of interest, the sensing system 104 can modify the frequencies and/or amplitudes that are measured from the vibrations of interest. For example, the sensing system 104 can decrease the frequencies at which peaks appear in the vibrations of interest 300, 306, 308, can decrease the amplitudes of the peaks in the vibrations of interest 300, 306, 308, or the like. The frequencies and/or amplitudes of the peaks in the vibrations of interest 300, 306, 308 can be decreased by the same amount that the frequencies and/or amplitudes of the peaks in the baseline vibrations 400, 404 increased, or may be decreased by an amount that is at least partially based on the increase in the peaks in the baseline vibrations 400, 404.

In one embodiment, the sensing system 104 can determine information about the environmental conditions based on the differences between the baseline vibrations. For example, based on decreases in frequency for one or more peaks in the baseline vibrations, the sensing system 104 can determine that the ground is becoming softer, such as due to rainfall. Alternatively, based on increases in frequency for one or more peaks in the baseline vibrations, the sensing system 104 can determine that the ground is becoming harder, such as due to ice forming on and/or in the ground. The sensing system 104 can use this information about the environmental conditions to change vibrations of interest, as described above. Additionally or alternatively, the sensing system 104 can use the information about the environmental conditions to warn operators of vehicles of dangerous conditions. For example, the sensing system 104 can generate signals that are communicated to vehicles to warn the vehicles of potential ice, rain, or the like, that the sensing system 104 may have detected.

Once the information determined from the vibrations of interest is corrected, the vibrations of interest can be referred to as corrected or modified vibrations of interest. For example, a waveform, measured frequency of a peak, measured amplitude of a peak, or the like, in the vibration of interest may be corrected by changing the measured waveform, measured frequency, and/or measured amplitude to a modified waveform, frequency and/or amplitude. This corrected or modified information can be compared to the signatures or waveforms associated with different objects of interest. Depending on which signatures or waveforms more closely match or otherwise correspond to the corrected or modified information, the sensing system 104 may be able to identify the object of interest, the speed of the object of interest, the location of the object of interest, the size of the object of interest, or the like, based at least in part on the corrected or modified information. The identified object, speed, location, size, or the like can be used for a variety of purposes, such as to activate a warning system or signal that a vehicle is approaching, to determine if a vehicle is traveling too fast or too slow, to generate control signals that automatically slow down or speed up the vehicle based on the speed that is determined, or the like. For example, based on the corrected information, the sensing system 104 can determine a size of a moving vehicle, the location of the vehicle, and/or how fast the vehicle is moving. The size of the vehicle may be used by the sensing system 104 to differentiate between different vehicles and thereby identify the vehicle. Based on the location of the vehicle and the speed of the vehicle, the sensing system 104 can generate control signals that are communicated to one or more locations, such as a dispatch center, where the identify, location, and/or speed of the vehicle can be displayed to one or more operators to monitor movements of the vehicle. Optionally, these control signals may be communicated to a signal (e.g., a light or a gate) to actuate the signal and warn other vehicles of the movement of the detected vehicle.

Figure 5:
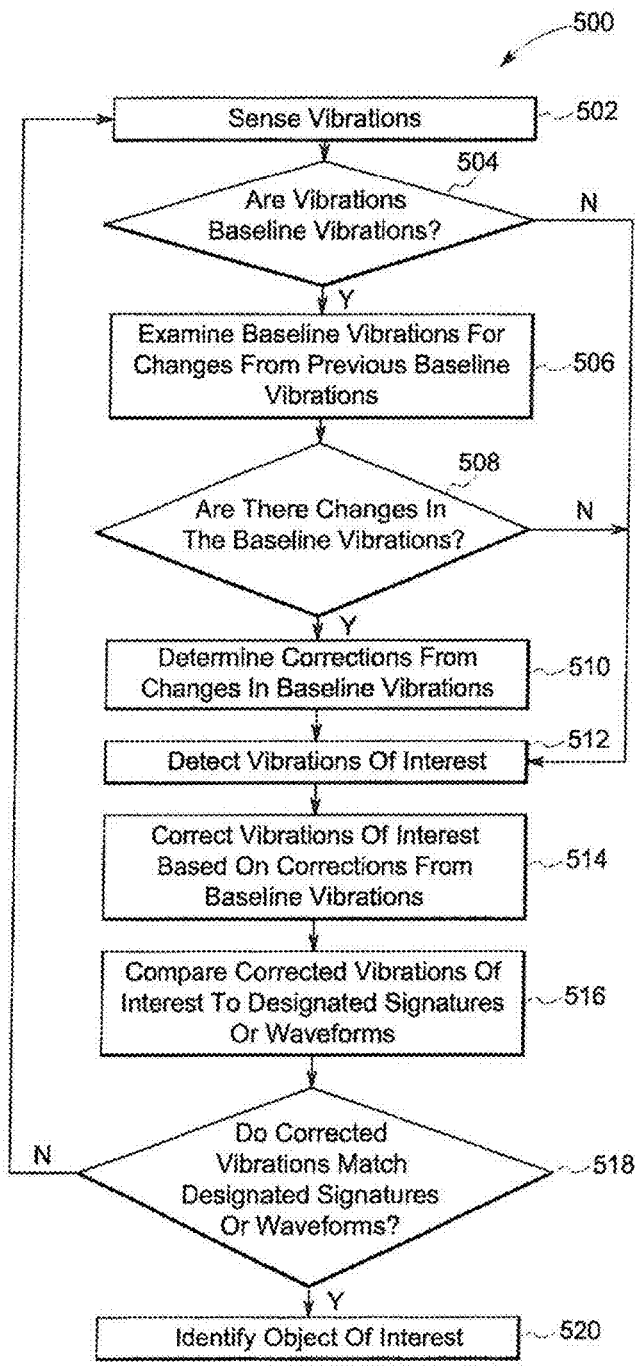
FIG. 5 illustrates a flowchart of a method for monitoring vibrations according to one embodiment.

FIG. 5 illustrates a flowchart of a method 500 for monitoring vibrations according to one embodiment. The method 500 can be performed by the monitoring system 100 shown in FIG. 1 and described above. At 502, vibrations are sensed. For example, vibrations propagating through the ground may be detected. The vibrations can be sensed by examining changes in light being conveyed through a cable, such as a fiber optic cable. Alternatively, the vibrations may be sensed in another manner, such as by using one or more accelerometers or other devices. At 504, a determination is made as to whether the sensed vibrations are baseline vibrations. The baseline vibrations may be generated at known or designated times, or within known or designated time periods. If the vibrations are sensed at the known or designated times, within a designated time period following the known or designated times (e.g., within thirty seconds or another time period), within the known or designated time periods, or the like, then the sensed vibrations may be identified as baseline vibrations. As a result, flow of the method 500 can proceed to 506. On the other hand, if the sensed vibrations are not sensed at times that would correspond with the generation of the baseline vibrations, then flow of the method 500 can proceed to 512, which is described below.

At 506, the baseline vibrations are examined for changes from one or more previous baseline vibrations. For example, the baseline vibrations sensed at 502 can be compared with previously sensed baseline vibrations to determine if shapes, waveforms, peaks, or the like, in the previously sensed baseline vibrations have moved (e.g., changed which frequencies the peaks appear at), changed shape (e.g., have larger or smaller amplitudes, are wider or narrower, etc.), or otherwise changed.

At 508, a determination is made as to whether the baseline vibrations have changed. If the baseline vibrations have changed from one or more previously sensed baseline vibrations, then environmental conditions may be altering the propagation of vibrations through the ground. As a result, the vibrations generated by objects of interest also may be altered by the environmental conditions in a similar manner. If the baseline vibrations have changed or have changed by at least a significant amount (e.g., the frequency of a peak changes by at least a designated, non-zero amount, such as 1%, 5%, 10%, or another amount), then flow of the method 500 can proceed to 510. On the other hand, if the baseline vibrations have not changed, or have not changed by a significant amount, then flow of the method 500 can proceed to 512, which is described below.

At 510, corrections to sensed vibrations are determined from the changes in the baseline vibrations. For example, the change in the frequencies at which one or more peaks appear in the baseline vibrations, the change in amplitudes of the peaks, or other changes, may be calculated. At 512, vibrations of interest are sensed. If the vibrations sensed at 504 are not baseline vibrations, then the sensing of vibrations at 504 and 512 may be the same operation of sensing the same vibrations. Because the vibrations are not baseline vibrations used to determine corrections to account for changing environmental conditions, the vibrations may be vibrations of interest. These vibrations may be used to identify an object of interest, speed of the object of interest, a location of the object of interest, or the like.

At 514, the vibrations of interest are corrected based on the corrections determined from the baseline vibrations. For example, one or more frequencies, amplitudes, waveforms, or the like, that are determined from the vibrations of interest can be modified based on the corrections determined from the baseline vibrations. If no corrections were determined based on changes in the baseline vibrations (e.g., the baseline vibrations were not affected by the environmental conditions or were not significantly affected such that one or more peaks did not shift frequencies and/or change amplitudes by at least a designated, non-zero amount), then the information obtained from the vibrations of interest may not be modified. On the other hand, if corrections were determined based on changes in the baseline vibrations, then these corrections may be applied to the information determined from the vibrations of interest to form corrected or modified information from the vibrations of interest.

At 516, the corrected vibrations of interest (or vibrations of interest that were not corrected due to the lack of significant changes to the baseline vibrations) are compared to one or more designated signatures or waveforms. As described above, different signatures or waveforms may include different patterns, arrangements, or the like, of peaks, and may be representative of different types of objects of interest, different moving speeds of different objects of interest, different locations of objects of interest, etc.

At 518, a determination is made as to whether the corrected vibrations of interest (or vibrations of interest that were not corrected due to the lack of significant changes to the baseline vibrations) match one or more of the signatures or waveforms. For example, a determination may be made as to whether the peaks or other shapes of the frequency spectrum of the corrected vibrations of interest more closely match the peaks or other shapes of a signature or waveform than one or more other signatures or waveforms. If so, then flow of the method 500 can proceed to 520. For example, the corrected vibrations of interest may closely match the peaks of a signature or waveform representative of a particular object of interest, a particular speed of an object of interest, a particular location of an object of interest, or the like. On the other hand, if the corrected vibrations of interest do not match one or more of the signatures or waveforms, then the vibrations of interest may not represent an object of interest, a speed of an object of interest, a location of an object of interest, or the like. As a result, flow of the method 500 can return to 502 for additional vibrations to be sensed.

At 520, information about an object of interest is determined based at least in part on the vibrations of interest. For example, the object of interest, the location of the object of interest, the speed of the object of interest, or the like, that is associated with a signature or waveform that more closely matches the corrected vibrations of interest than other signatures or waveforms may be identified. After this identification, flow of the method 500 can return to 502 so that additional vibrations can be sensed, corrected, and/or used to identify information about an object of interest.

Returning to the description of the vibration monitoring system 100 shown in FIG. 1, the system 100 can adapt to changes in the location of the sensing device 106 and/or other components of the sensing system 104 by continuously and repeatedly verifying integrity of the sensing device signals. Accordingly, in another aspect, the system 100 may also include a calibration device 122 that is placed in the vicinity of the sensing device 106 and which can be utilized by the system 100 as a vital way to ensure that movements in either the calibration device 122 or the sensing device 106 and/or other components of the sensing system 104 are detected and accounted for. The calibration device 122 may interface with a wayside bungalow 124 containing communication equipment that relays health information of the calibration device 122 to the sensing processor 112. While the calibration device 122 and wayside bungalow 124 are illustrated as being separate from control system 102, in an embodiment, the calibration device 122 and wayside bungalow 124, including the communication equipment contained therein, may be integrated with the control system 102. By integrating the calibration device and communication equipment with the control system 102, duplication of components performing related functions may be obviated.

In one embodiment, the calibration device 122 includes an acoustic device configured to generate and amplify an analog tone 126 that propagates, through air and/or subterrain, to the sensing device 106, and is utilized as a regular calibration or reference point, as discussed hereinafter. The acoustic device may be, for example, a low frequency acoustic transducer that is configured to impart a low frequency acoustic signal (e.g., 1 to 30 Hz) to ground or otherwise. Alternatively or additionally, the acoustic device may utilize so-called ground penetrating sonar, such as described in U.S. Pat. No. 5,719,823, issued Feb. 17, 1998 and incorporated by reference herein in its entirety. Part of the acoustic device may be buried in the ground surface to facilitate transmission of acoustic energy from the device to soil. Additionally, soil around the buried portion may be made uniform or otherwise augmented to facilitate transfer of acoustic energy from the buried portion to non-augmented soil in which the fiber optic cable is buried.

The calibration device 122 may be installed on a moving platform or fixed anywhere along the wayside route and provides a reference point or location point through either a mile post marking, survey marker, GPS, or other known reference point. The exact location of the calibration device 122 is stored by the sensing processor 112 as a repeatable reference point and verified as needed for system integrity checking. Once calibrated, a window threshold may be set and, when exceeded, the system 100 will be alerted that the sensing device 106 has moved or the calibration device 122 has moved or is being interfered with. In an embodiment, the calibration device 122 may send a continuous signal to the sensing device 106. In other embodiments, the calibration device 122 may output the reference tone 126 at defined intervals.

In particular, in one embodiment, the calibration device 122 may have an on-board, real-time precision clock 128. Embedded software/firmware utilizes the on-board clock 128 to energize the acoustic output at defined intervals. The device 122 has communication abilities, which allow for the syncing of the device 122 with a wayside location or to the back office to ensure drift of the clock 128 is accommodated.

In another embodiment, the calibration device 122 receives communication protocol at regular intervals in the event that the system 100 needs to verify the accuracy and location of the device 122. The calibration device 122 will then generate the analog signal, and report back to the sensor processor 112 once it has generated the signal. The sensor processor 112 will then confirm that a signal was received both from the sensors 110 as well as the status from the calibration device 122 to confirm the output was successfully energized.

In the event that the sensing device 106 is moved, and to prevent a false positive signal from the calibration device 122 to the sensing device 106, the calibration device 122 is provided as a constant power output device that monitors the output signal 126 and ensures that a failure mode of the device does not falsely output an increase in energy or signal level such that the sensing device 106 will detect the reference signal from a greater distance away.

The calibration device 122 may be arranged within a housing (not shown) capable of withstanding the harsh environment of an external wayside (e.g., rail) location. In certain embodiments, the calibration device 122 accepts either standard DC or AC input to energize the device using common connector types such as Wago or Phoenix, and has the ability to communicate either fiber optically or over Ethernet back to a wayside bungalow 126 or back office to report the status of the device 122 as a form of health indication and monitoring.

FIG. 6 illustrates a flowchart of a method 600 for verifying the integrity of the sensing system 104. The method 600 can be performed by the monitoring system 100 shown in FIG. 1 and described above. At 602, the sensing processor 112 continuously monitors the sensing device 106 for signals, in the manner described above, to determine vehicle movement or for calibration information generated by the calibration device 122. At step 604, the calibration device outputs an analog signal to be received by the sensing device 106 at a given location. At step 606, the sensing processor 112 receives the signal generated by the calibration device 122 through the sensing device 106. The sensing processor 112, at step 608, then verifies that the signal level of the received signal is within a predetermined threshold, which signifies that the calibration device 122 and the sensing device 106 have not moved.

FIG. 7 illustrates a flowchart of a method 700 for determining the location status of the calibration device 122. The method 700 can be performed by the monitoring system 100 shown in FIG. 1 and described above. At step 702, the calibration device 122 may utilize GPS or other time-based location to determine status. Mile post may also be programmed into the calibration device 122. At step 704, the calibration device 122 syncs with the sensing processor 112 or wayside equipment to confirm date, time and location. At step 706, the acoustic signal sent through the sensing device 106 is utilized to verify that the sensing device (i.e., the fiber optic cable) has not moved and the calibration device 122 has not moved. If the sync does not occur or the sensing processor 112 determines that the signal level is unacceptable (e.g., outside of a predefined threshold window), the sensing processor 112 will alert the system 100, at step 708, that the calibration device 122 cannot be trusted.

As discussed above, to ensure the safety integrity level is maintained and the calibration device 122 has not been relocated, the calibration device 122 includes a form of self-location, such as GPS or other time-based synchronization system similar to that contained in aircraft navigation systems. This self-location information may be communicated either to the fiber interrogation equipment (i.e., the sensing processor 112) or stored in the sensing processor 112 which will validate the reported position versus the allowable position. This will provide notification in the instance that the calibration device 122 has been moved to maintain vitality of the system 100.

In one embodiment, a system includes an acoustic device that outputs an analog signal to a fiber cable for calibration and location verification. The acoustic device utilizes GPS or communication from wayside bungalow equipment to verify GPS location or real-time clock information. The wayside bungalow contains communication equipment that interfaces with the acoustic device and relays health information to a sensing processor. The sensing processor is configured to detect the acoustic signal output by the acoustic device at a known location and verifies that the cable and device have not moved location by comparing the signal level received against a threshold stored in memory. When the threshold is exceeded, the sensing processor sends an alert that the fiber optic cable or acoustic device at the location have changed.

FIG. 8 is a schematic diagram of a vibration monitoring system 800, i.e. of a detecting system for detecting the presence of a vehicle on a railway track, according to one embodiment. The detecting system 800 includes a control system 802 configured for generating and emitting signals into the ground 808. The signals correspond for example to vibrations produced into the ground and/or to analog tones. The signals correspond notably to baseline vibrations that are used to detect changes in environmental conditions and/or initialization vibrations that are used to initialize a sensing system 804 of the detecting system, and/or analog tones that propagate, through air and/or sub-terrain, to the sensing system 804 and are utilized as a regular calibration or reference point.

The sensing system 804 is adapted for detecting vibration into ground and notably for detecting vehicles circulating on the track inducing second signals, i.e. vibrations of interest, also called second signals.

The sensing system 804 is also adapted for detecting first, third and fourth signals corresponding respectively to initialization vibrations V1 that are used to initialize the sensing system 804, analog tones used to detect if the control system or the sensing system has moved in an unexpected manner, baseline vibrations V2 that are used to detect changes in environmental conditions.

The sensing system 804 comprises a sensing device 806 and sensors 810 (810A, 810B, 810C) comprising respectively the same elements, arranged in a same manner, than the sensing system 104 and the sensing device 106, described above in the first embodiment described.

The sensing system 804 is associated with a sensing processor 812, also called sensing module, monitoring the sensing system 804, the sensing processor comprising the same elements, arranged in a same manner, than the sensing processor 112, described above in the first embodiment described.

The control system 802 comprises a controller 822 that represents one or more computer processors (e.g., microprocessors), hardware circuits or circuitry, or a combination thereof, which is associated with a central memory 824.

Advantageously the controller 822 is adapted for executing software programming instructions comprised in the central memory 824.

The control system 802 comprises a moving object 830 adapted for generating vibrations into the ground and notably baseline vibrations V2 that are used to detect changes in environmental conditions of the track and initialization vibrations V1 that are used to initialize the sensing processor 812.

The control system 802 comprises an actuator 832 configured for controlling the movement of the moving object 830. Advantageously, the actuator comprises two functioning mode a track configuration mode in which it commands the moving object to emit the first signal corresponding to the initialization vibrations V1 and a supervision mode in which it commands the moving object to emit the fourth signal corresponding to the baseline vibrations V2.

The control system 802 comprises also a communication device 836 adapted for communicating data and notably exchanging messages with the sensing processor 812 and a calibration device 838 corresponding to the calibration device 122 described above. The calibration device 838 is adapted for sending the third signal corresponding to an analog tone T1 that propagates, through air and/or sub-terrain, to the sensing system 804 and is utilized as a regular calibration or reference point.

Advantageously the control system 802 comprises a localization device 839, such as a GPS device, adapted for determining the position of the control system 802.

The control system 802 is preferably movable and mounted on wheels, in order that an operator can move the control system 802 along the railway track.

Advantageously the control system 802 is adapted to be taken off the wheels and installed along the track close to a sensing system 804 after the initialization of the sensing processor 812.

The sensing processor 812 comprises a detection module 840 for detecting a vehicle on the railway track, a configuration device 842 adapted for configuring the detection module 840, a security module 844 to determine if at least one of the calibration device 838 or the sensing device 806 has moved and a control module 846 adapted for supervising changes in the environmental conditions of the sensing system 804.

The central memory 824 comprises initialization programming instructions 850 and controlling programming instructions 856.

The initialization programming instructions 850 and the controller 822 form with the moving object 830, the actuator 832 and the communication device 836 an initialization device.

The initialization programming instructions 850 are configured, while they are executed, to command the actuator 832, to emit the first signal into the ground 808 towards the sensing processor 812 through the sensing device 806, which is for example a fiber optic cable.

The initialization programming instructions 850 are also configured, while they are executed, to generate a first message comprising configuration data chosen among, location of the initialization device, intensity/magnitude of the first signal, emission time of the first signal and type of objects corresponding to the first signal, and to command the sending of the first message to the sensing processor 812 through the communication device 836.

Advantageously, the configuration data comprise at least the first signal intensity/magnitude.

Preferentially, the initialization programming instructions 850 are configured for commanding the emission of the first signal and the sending of the first message approximately simultaneously.

Advantageously, the controller 822 is adapted for executing the initialization programming instructions 850 several times for a given location of the control system 802, in order to successively emit different first signals having different intensity levels. The initialization programming instructions 850 are for example executed at predetermined time intervals, or each time an activator on the control system is activated, or when the initialization device is not moving for a predetermined amount of time.

The fact that the control system 802 can send the first signal at times that are known to the sensing system 804 and notably communicated to the sensing system 804 allows to differentiate first signals from other signals.

The controlling programming instructions 856 are configured, while they are executed, to command the actuator 832, to send the fourth signal into the ground towards the sensing processor 812 through the sensing device 806 which is for example a fiber optic cable.

The controlling programming instructions 856 are also configured, while they are executed, to generate a second message comprising control data chosen among, location of the control system 802, intensity/magnitude of the fourth signal, emission time of the fourth signal, and to command the sending of the second message to the sensing processor 812 through the communication device 836.

Preferentially, the controlling programming instructions 856 are configured for commanding the emission of the fourth signal and the sending of the second message approximately simultaneously.

Advantageously, the fourth signal is outputted at predetermined times and/or during predetermined time periods, the fourth signal having advantageously a predetermined amplitude, i.e. intensity/magnitude, and/or frequency.

The fact that the control system 802 can send the fourth signal at times that are known to the sensing system 804 and notably communicated to the sensing system 804 and with specific amplitude and/or frequency allows to differentiate fourth signals from other signals.

The calibration device 838 is configured for outputting the third signal towards the sensing processor 812 through the sensing device 806.

Advantageously the intensity/magnitude of the third signal is predetermined for a given location of the control system and the sensing processor.

The calibration device 838 includes an acoustic device 860 configured to generate and amplify the analog tone that propagates, through air and/or sub-terrain, to the sensing device, and is utilized as a regular calibration or reference point, as discussed hereinafter. The acoustic device may be, for example, a low frequency acoustic transducer that is configured to impart a low frequency acoustic signal (e.g., 1 to 30 Hz) to ground or otherwise. Alternatively or additionally, the acoustic device may utilize so-called ground penetrating sonar, such as described in U.S. Pat. No. 5,719,823, issued Feb. 17, 1998 and incorporated by reference herein in its entirety. Part of the acoustic device may be buried in the ground surface to facilitate transmission of acoustic energy from the device to soil. Additionally, soil around the buried portion may be made uniform or otherwise augmented to facilitate transfer of acoustic energy from the buried portion to non-augmented soil in which the fiber optic cable is buried.

The calibration device 838 is adapted for providing a reference point or location point to the sensing processor thanks to the localization device 839 and the communication device 836. The exact location of the calibration device is stored by the sensing processor as a repeatable reference point and verified as needed for system integrity checking. For example, the calibration device 838 is adapted for sending to the sensing processor 812 the position of the control system 802 determined by the localization device 839. Once calibrated, a window threshold may be set in the sensing processor 812 and, when intensity/magnitude level of the third signal exceeded, the security module 844 is adapted to determine that the sensing device has moved or the calibration device has moved or is being interfered with. The window threshold may depend on the control system position sent by the control system 802. In an embodiment, the calibration device 838 may send the third signal continuously to the sensing device 806. In other embodiments, the calibration device 838 may output the third signal, i.e. the reference tone at defined intervals and approximately at the same time send the location of the control system 802 to the sensing processor 812.

Advantageously, the frequency of the third signal is not comprised in the frequency spectrum of the first and fourth signals so that the sensing processor 812 can differentiate the three signals.

More advantageously, the first, third and fourth signals are emitted at times that are known or communicated to the sensing processor 812 (e.g., by the control system 802) and with predefined frequency spectrum and intensity/magnitude intervals so that the sensing processor 812 can differentiate between first, third, fourth signals and second signals, corresponding to a second signal induced by a vehicle moving on the track close to the sensing system 804.

The configuration device 842 is adapted for configuring the detection module 840 in function of the received first signal and the received configuration data.

The configuration device 842 is notably adapted for memorizing in a comparison unit 870 of the detection module 840 a set of measured data relative to the received first signal and to associate to the memorized set of measured data the received configuration data.

Advantageously when the configuration device 842 received several first signals having the same intensity and sent from the same location it determines the set of measured data to memorize in function of the different first signals received, by performing for example an averaging algorithm.

Advantageously in the comparison unit 870, the memorized set of measured data is associated with a type of detected object, according to the signal intensity comprised in the associated configuration data and preferentially is associated also with a location of the type of detected object determined in function of the location of the initialization device comprised in the configuration data.

The comparison unit 870 memorizes, for example, a set of measured data for each first signal received having a different value of signal intensity comprised in the associated configuration data and/or a different location comprised in the associated configuration data.

The sensing processor 812 and notably the comparison unit 870 is configured for comparing a received second signal, generated by an object moving near the sensing processor, with each memorized set of measured data in order to determine a type of detected object circulating on the railway track and preferentially also its location.

More advantageously, the memorized set of measured data is relative to a general form of the first signal monitored by the sensing processor 812 through the sensing device 806 and corresponds to a signal signature or waveform which is associated with a type of detected object, notably in function of the signal intensity/magnitude comprised in the associated configuration data. The signatures or waveforms may be defined as designated peaks that are located at designated frequencies and/or within a designated range of frequencies.

If the vibrations of interest, i.e. the second signals, have peaks in the designated frequencies and/or designated range of frequencies, then the vibrations of interest may be identified as the object of interest that is associated with the designated frequencies and/or designated range of frequencies of the set of measured data. Optionally, different objects of interest may be associated with different set of measured data, different speeds of different objects of interest may be associated with different set of measured data, different locations of objects of interest may be associated with different set of measured data, and the like, so that the sensing system 804 and notably the detection module 840 may be able to identify different objects of interest, different speeds of objects of interest, different locations of the objects of interest, and the like comparing second signals with memorized sets of measured data.

Depending on which set of measured data, i.e. signatures or waveforms more closely match or otherwise correspond to the received second signal, the sensing processor 812 may be able to identify the object of interest, the speed of the object of interest, the location of the object of interest, the size of the object of interest, or the like.

The security module 844 is adapted for comparing the third signal amplitude with a window threshold to determine if at least one of the calibration device or the sensing device 806 has moved. When intensity level of the third signal exceeds the window threshold, the security module 844 is adapted to determine that the sensing device has moved or the calibration device has moved or is being interfered with.

The calibration device 838 and the security module are, for example, adapted for implementing the method 700.

The control module 846 is adapted for supervising changes in the environmental conditions of the sensing system 804. The control module 846 is notably configured for comparing the received fourth signal with pre-memorized data in order to detect changing in environmental conditions of the railway track.

The control module 846 is adapted for amending the memorized set of measured data or data relative to a received second signal in function of the detected changes in environmental conditions of the railway track. The control module 846 is adapted to obtain information about environmental conditions and detect changes as described for the sensing processor 112 above. The baseline vibrations 400 can be for example designated as a calibration signature. The sensing processor 812 may periodically, regularly, randomly, or otherwise repeatedly re-determine the baseline vibrations that are used as the calibration signature. Subsequently obtained baseline vibrations 402, 404 through sensing device 806 can be compared to the calibration signature in order to determine how the vibrations sensed by the sensing system 804 change due to the changing environmental conditions. For example, the control module 846 can sense the baseline vibrations 402 and compare the baseline vibrations 402 to the baseline vibrations 400 by comparing characteristics of the vibrations 400, 402 with each other. These characteristics can include, but are not limited to, locations (e.g., frequencies) of peaks 406 (e.g., peaks 406A-H), widths of the peaks 406 (e.g., the ranges of frequencies over which one or more peaks 406 extend, heights of peaks 406 (e.g., the amplitude of one or more of the peaks 406 along the vertical axis 304), and the like.

In one embodiment, the control module 846 is adapted for amending a received second signal, induced by a vehicle moving on the track close to the sensing system 804, in function of the detected changes in environmental conditions of the railway track.

The control module 846 can use differences between the baseline vibrations 400, 402 to correct data relative to received second signals, that are determined from the vibrations of interest 300, 306, 308 shown in FIG. 3. For example, due to changing environmental conditions, the baseline vibrations 400, 402 appear to shift to lower frequencies and/or have reduced amplitudes, as described above. To correct for the impact of the changing environmental conditions on the vibrations of interest, the control module 846 can measure frequencies and/or amplitudes from the vibrations of interest, and then modify these frequencies and/or amplitudes. For example, the control module 846 can increase the value of the measured frequencies at which peaks appear in the vibrations of interest 300, 306, 308, can increase the value of the amplitudes of the peaks in the vibrations of interest 300, 306, 308, or the like. The frequencies and/or amplitudes of the peaks in the vibrations of interest 300, 306, 308 can be increased by the same amount that the frequencies and/or amplitudes of the peaks in the baseline vibrations 400, 402 decreased, or may be increased by an amount that is at least partially based on the decrease in the peaks in the baseline vibrations 400, 402.

The control module 846 can repeatedly monitoring changes in baseline vibrations generated by the control system 802 to monitor changes in the environmental conditions and using these changes to modify (e.g., correct) the information that is determined from the vibrations of interest generated by an object 200 circulating close to the sensing system 804.

In one aspect, the control module 846 is configured to determine that the system 100 is malfunctioning based at least in part on the baseline vibrations. For example, the sensing control module 846 may be aware of the times at which the baseline vibrations are generated by the control system 802. If the control module 846 does not detect the baseline vibrations at times that correspond to when the baseline vibrations are generated, then the control module 846 can determine that the system 800 is malfunctioning. Responsive to determining this, the sensing processor 812 can communicate one or more warning signals to another location, such as a repair facility, dispatch facility, or the like, to warn of the malfunction of the system 800, and/or to request inspection, repair, maintenance, or the like, of the system 800.

As a variant, the initialization programming instructions 850 are configured, while they are executed, to command the actuator 832, to emit successively several first signals having the same intensity levels, while the control system stays preferably at the same location. In this variant the memorized set of measured data are determined by using averaging algorithm for example.

As a variant, the control system 802 is devoid of calibration device and the actuator comprises only one functioning mode which is the track configuration mode. In this variant after the initialization of the sensing processor 812, control systems 102 are installed along the track for each sensing system 804 and functions has described in the first embodiment described above. In this variant, the memorized sets of measured data correspond to the designated signatures or waveforms of FIG. 5.

Figure 9:
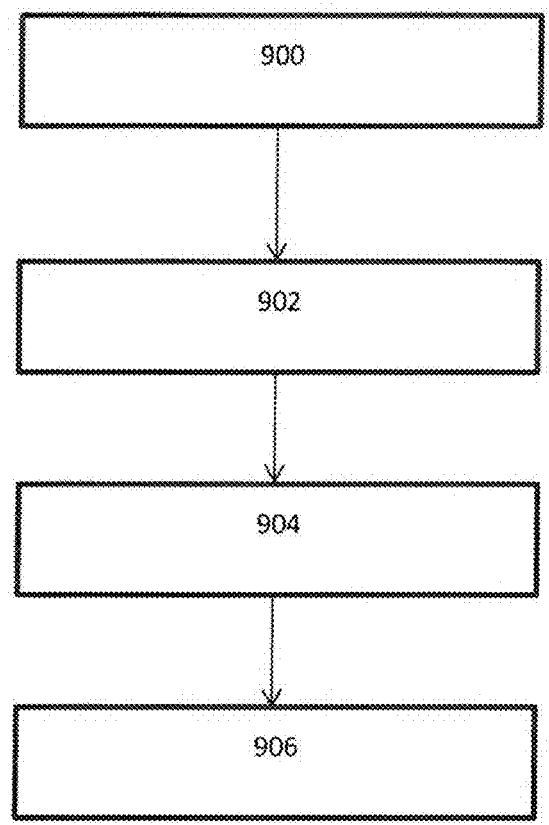
FIG. 9 illustrates a flowchart of the steps of a method for detecting the presence of a vehicle on a railway track according to one embodiment of the invention realized by the detecting system of FIG. 8.

FIG. 9 illustrates a flowchart of the steps of a method for detecting the presence of a vehicle on a railway track realized by the detecting system 800.

First, the method comprises an initialization step 900, then after the finalization of the initialization step the method comprises, a security step 902, a control step 904 and a detecting step 906.

Figure 10:
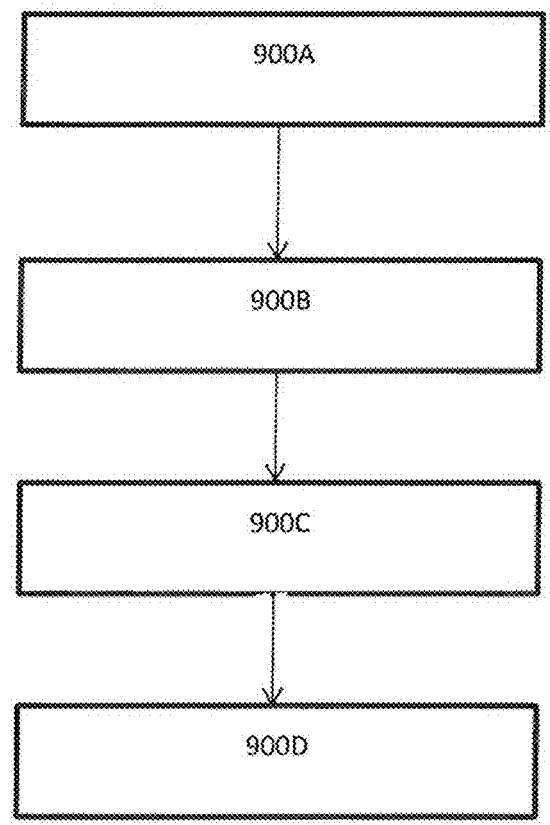
FIG. 10 illustrates a flowchart of the sub-steps of an initialization step of the method of FIG. 9.

The initialization step is presented in more details on FIG. 10. The initialization step comprises:
an emission sub-step 900A, during which, the controller executes the initialization programming instructions 850 in order to emit the first signal;
a sending sub-step 900B, the controller 822 executing the initialization programming instructions 850 in order to send the first message to the sensing processor 812;
a monitoring sub-step 900C, the sensing processor 812 monitoring the sensing system; and
a configuring sub-strep 900D, during which the configuration device 842 configures the detection module 840 in function of the received first signal and the received configuration data. More especially, a set of measured data relative to the received first signal are memorized and are associated with the configuration data and notably with a type of detected object, according to, for example, the signal intensity comprised in the associated configuration data. Preferentially the memorized set of measured data is associated also with a location of the type of detected object determined in function of the location of the control system 802 comprised in the configuration data.

During the initialization step the actuator 832 is configured in the track configuration mode.

After the initialization, step the sensing processor 812 is initialized and is configured for detecting objects moving on the track close to the sensing system 804. Advantageously, after the initialization step the control system 802 is taken off the wheels and installed close to the sensing system 804 at a predetermined location.

After the initialization step the actuator 832 is configured in the supervision mode.

Advantageously, the initialization step 900 is repeated: at predetermined time intervals, or each time an activator on the initialization device is activated, or when the initialization device is not moving for a predetermined amount of time.

Advantageously the control system 802 is moved along the track at predetermined locations and the initialization step 900 is repeated several times with first signals having different intensity levels, corresponding to different type of objects, such as a car, an animal, a train, a road vehicle . . .

Figure 11:
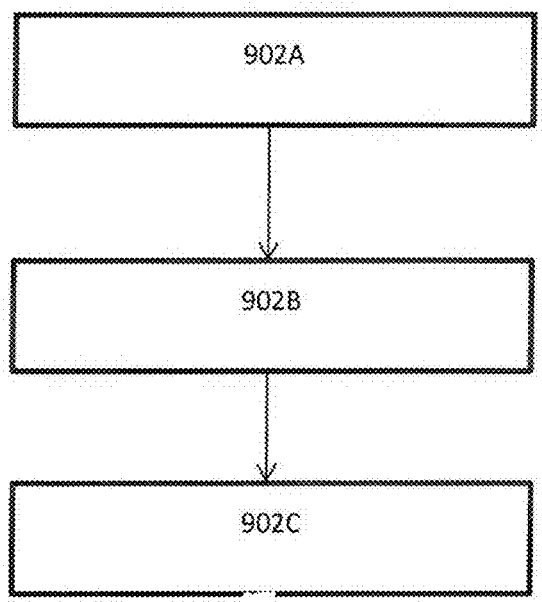
FIG. 11 illustrates a flowchart of the sub-steps of a security step of the method of FIG. 9.

The security step 902 is presented in more details on FIG. 11. The security step 902 comprises:
a sending sub-step 902A, during which the calibration device output the third signal;
a monitoring sub-step 902B, the sensing processor monitoring the sensing system; and
a determining step 902C, during which the security module compares the third signal amplitude with a window threshold to determine if at least one of the calibration device or the sensing device 806 has moved. When intensity level of the third signal exceeds the window threshold, the security module 844 determines that the sensing device has moved or the calibration device has moved. Thus, this determining sub-step includes verifying if at least one of the calibration device or sensing system has moved.

Advantageously, when the window threshold is exceeded, the sensing processor 812 sends an alert, that the fiber optic cable or acoustic device at the location have changed, to a supervision central of the railway track.

Figure 12:
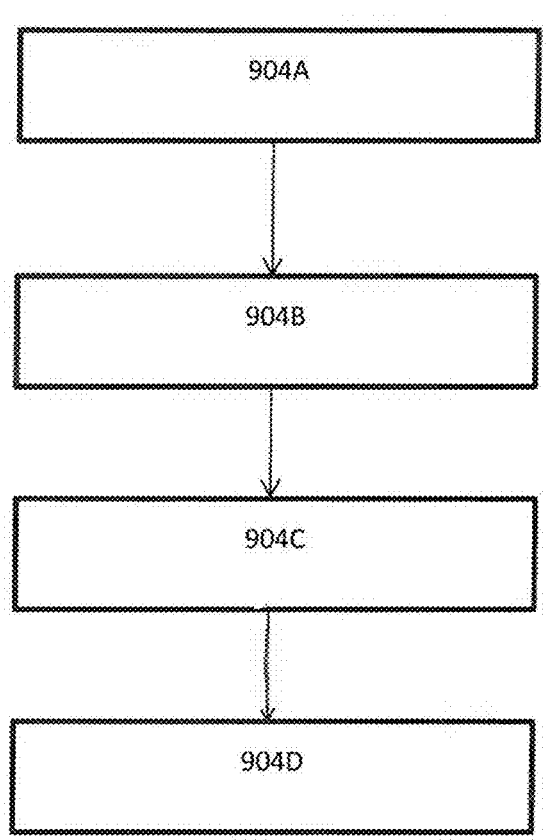
FIG. 12 illustrates a flowchart of the sub-steps of a control step of the method of FIG. 9.

The control step 904 is presented in more details on FIG. 12. The control step 904 comprises:
an emitting sub-step 904A, during which the control system 802 output the fourth signal;

a sending sub-step 904B, the control system 802, sending to the sensing processor 812, a second message comprising control data chosen among, location of the control device, intensity/magnitude of the fourth signal, emission time of the fourth signal;

a monitoring sub-step 904C, the sensing processor monitoring the sensing system;

a modifying sub-step 904D, during which the sensing processor modifies the memorized set of measured data or measured data relative to a received second signal in function of the received fourth signal. During the modifying sub-step the sensing processor compares the received fourth signal with pre-memorized data in order to detect changing in environmental conditions of the railway track, then at least one of the memorized set of measured data or measured data relative to the received second signal being modified in function of the detected changes in environmental conditions of the railway track.

Figure 13:
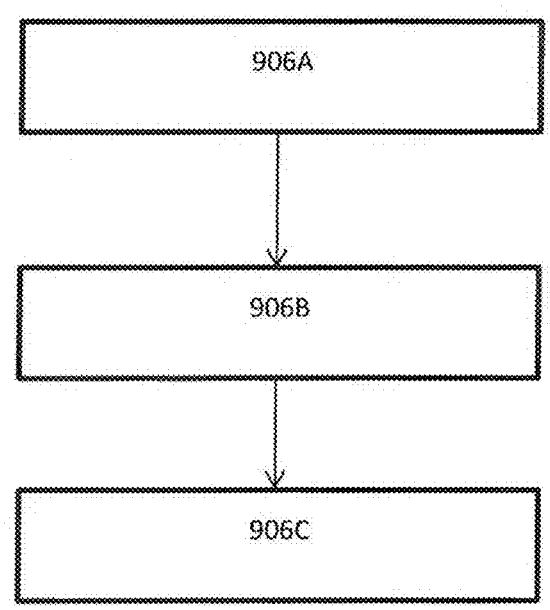
FIG. 13 illustrates a flowchart of the sub-steps of a detecting step of the method of FIG. 9.

The detecting step 906 is presented in more details on FIG. 13. The detecting step 906 comprises:

a commissioning step 906A, during which an object, notably a train, moves on the track close to the sensing system; The movement of the train induces vibrations corresponding to a second signal measured by the sensing system, a monitoring sub-step 906B, the sensing processor monitoring the sensing system; and a determination sub-step 906C, during which the sensing processor compares the received second signal with each memorized set of measured data in order to determine a type of detected object circulating on the railway track and preferentially also its location.

Advantageously, before the determination sub-step, the control step 904 is realized to amend the measured data relative to a received second signal in function of detected changes in environmental conditions.

At step 904C, for example, a determination may be made as to whether the peaks or other shapes of the frequency spectrum of the vibrations of interest more closely match the peaks or other shapes of a signature or waveform than one or more other signatures or waveforms. For example, the corrected vibrations of interest may closely match the peaks of a signature or waveform representative of a particular object of interest, a particular speed of an object of interest, a particular location of an object of interest, or the like. On the other hand, if the corrected vibrations of interest do not match one or more of the signatures or waveforms, then the vibrations of interest may not represent an object of interest, a speed of an object of interest, a location of an object of interest, or the like. Then, flow of the method can return to 906A and 906B for additional vibrations to be sensed.

At step 904C, information about an object of interest is determined based at least in part on the vibrations of interest. For example, the object of interest, the location of the object of interest, the speed of the object of interest, or the like, that is associated with a signature or waveform that more closely matches the corrected vibrations of interest than other signatures or waveforms may be identified.

Therefore, it appears that the control step 904 impact the detecting step 906 and allows to adapt the detecting step to changes in environmental conditions of the railway track.

Clearly, the principle of the invention remaining the same, the embodiments and the details of production can be varied considerably from what has been described and illustrated purely by way of non-limiting example, without departing from the scope of protection of the present invention as defined by the attached claims.

Components of the systems described herein may include or represent hardware circuits or circuitry that include and/or are connected with one or more processors, such as one or more computer microprocessors. The operations of the methods described herein and the systems can be sufficiently complex such that the operations cannot be mentally performed by an average human being or a person of ordinary skill in the art within a commercially reasonable time period. For example, the examination of the vibrations may take into account a large amount of information, may rely on relatively complex computations, and the like, such that such a person cannot complete the examination of the vibrations within a commercially reasonable time period to correct vibrations measured during passage of a vehicle. The hardware circuits and/or processors of the systems described herein may be used to significantly reduce the time needed to obtain and examine the vibrations.

As used herein, a structure, limitation, or element that is "configured to" perform a task or operation is particularly structurally formed, constructed, programmed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, programming of the structure or element to perform the corresponding task or operation in a manner that is different from an "off-the-shelf" structure or element that is not programmed to perform the task or operation, and/or denotes structural requirements of any structure, limitation, or element that is described as being "configured to" perform the task or operation.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. As used herein, the terms "including" and "in which" are used as the plain-English equivalents of the respective terms "comprising" and "wherein." Moreover, as used herein, the terms "first," "second," and "third," etc. are used merely as labels, and are not intended to impose numerical requirements on their objects.

This written description uses examples to disclose several embodiments of the inventive subject matter and also to enable a person of ordinary skill in the art to practice the embodiments of the inventive subject matter, including making and using any devices or systems and performing any incorporated methods. The patentable scope of the inventive subject matter may include other examples that occur to those of ordinary skill in the art. Such other examples are intended to be within the scope of the clauses if they have structural elements that do not differ from the literal language of the clauses, or if they include equivalent structural elements with insubstantial differences from the literal languages of the clauses.

The foregoing description of certain embodiments of the inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "an embodiment" or "one embodiment" of the inventive subject matter are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

What is claimed is:

1. A method for detecting the presence of an object on a railway track, using a sensing processor monitoring a sensing system for detecting vibration propagating through the ground, said sensing system being installed along the railway track and said sensing processor detecting the object on the railway track, the method comprising an initialization step comprising the sub-steps of:
   by an initialization device, emitting a first signal to be received by the sensing processor through the sensing system;
   by the initialization device, sending to the sensing processor, a first message comprising configuration data selected from the group consisting of: location of the initialization device, intensity of the first signal, emission time of the first signal, type of object corresponding to the first signal;
   by the sensing processor, monitoring the sensing system; and
   by the sensing processor, differentiating the first signal form a second signal induced by the object moving on the track based on the received first signal and the received configuration data.

2. The method of claim 1, wherein the sensing system comprises a fiber optic cable.

3. The method of claim 1, wherein the emitting and sending sub-steps are approximately realized simultaneously.

4. The method of claim 1, wherein the configuration data is the first signal intensity and during the configuring sub-step a set of measured data relative to the received first signal are memorized and are associated with the configuration data.

5. The method of claim 4, wherein the method comprises a control step comprising sub-steps of:
   by a control device, outputting a fourth signal to be received by the sensing processor through the sensing system; and
   by the sensing processor, modifying at least one of the memorized set of measured data or data relative to a received second signal based on of the received fourth signal.

6. The method of claim 5, wherein following the outputting of the fourth signal the control step comprises the following sub-step:
   by the control device, sending to the sensing processor, a second message comprising control data selected from the group consisting of: location of the control device, intensity of the fourth signal, and emission time of the fourth signal.

7. The method of claim 5, wherein the fourth signal is outputted at predetermined times and/or during predetermined time periods, the fourth signal having a predetermined intensity and/or frequency.

8. The method of claim 5, wherein during the modifying sub-step the sensing processor compares the received fourth signal with memorized data in order to detect changing in environmental conditions of the railway track, the at least one of the memorized set of measured data or data relative to the received second signal being modified based on the detected changing in environmental conditions of the railway track.

9. The method of claim 4, wherein during the configuring sub-step the memorized set of measured data is associated with a type of detected object, according to the signal intensity comprised in the associated configuration data and is associated also with a location of the type of detected object determined based on the location of the initialization device comprised in the configuration data.

10. The method of claim 9, wherein following the initialization step, the method comprises a detecting step comprising the sub-steps of:
    by the sensing processor, monitoring the sensing system; and
    by the sensing processor, comparing one or more received second signal with the memorized set of measured data in order to determine a type of detected object circulating on the railway track and preferentially also its location.

11. The method of claim 4, wherein the memorized set of measured data is relative to a general form of the first signal monitored by the sensing processor through the sensing system and corresponds to a signal signature associated with a type of detected object.

12. The method of claim 4, wherein following the initialization step, the method comprises a detecting step comprising the sub-steps of:
    by the sensing processor, monitoring the sensing system; and
    by the sensing processor, comparing one or more received second signal with each memorized set of measured data in order to determine a type of detected object circulating on the railway track and preferentially also its location.

13. The method of claim 1, wherein the initialization step is realized several times for a given location of the initialization device, different first signals having different intensity levels being successively emitted, the initialization device being moved along the track during the initialization step.

14. The method of claim 13, wherein following the initialization step, the method comprises a detecting step comprising the sub-steps of:
    by the sensing processor, monitoring the sensing system; and by the sensing processor, comparing one or more received second signal with each memorized set of measured data in order to determine the type of object circulating on the railway track and preferentially also its location.

15. The method of claim 1, wherein during the emitting sub-step several first signals having the same intensity levels are successively emitted, while the initialization device staying at the same location and wherein during the configuring sub-step the sensing processor is configured based on the received first signals and the received configuration data.

16. The method of claim 1, wherein the initialization device is movable along the railway track.

17. The method of claim 1, wherein the initialization step is repeated: at predetermined time intervals, or each time an activator on the initialization device is activated, or when the initialization device is not moving for a predetermined amount of time.

18. The method of claim 1, wherein the method comprises a security step comprising sub-steps of:
   by a calibration device, outputting a third signal having a predetermined characteristic to be received by the sensing processor through the sensing system;
   by the sensing processor, monitoring the sensing system; and
   by the sensing processor, determining if said characteristic of the signal from the calibration device has a value within a predetermined threshold window.

19. The method of claim 18, wherein:
   the sub-step of determining if the signal level of the third signal is within the predetermined threshold includes verifying if at least one of the calibration device or sensing system has moved.

20. The method of claim 1, wherein the first signal is an acoustic signal and a vibration signal sent into the ground.

21. A detecting system for detecting the presence of an object on a railway track, comprising:
   a sensing system for detecting vibration propagating through the ground, said sensing system being installed along the railway track,
   a sensing processor configured to monitor the sensing system and to detect the object on the railway track, and
   an initialization device configured to emit a first signal to be received by the sensing processor through the sensing system and to send to the sensing processor a first message comprising configuration data selected in the group comprising: location of the initialization device, intensity of the first signal, emission time of the first signal,
   wherein the sensing processor is configured to differentiate the first signal from a second signal induced by the object moving on the track based on the received first signal and the received configuration data.

* * * * *